(12) United States Patent
Strohbehn et al.

(10) Patent No.: US 8,173,174 B2
(45) Date of Patent: *May 8, 2012

(54) SOLUBILIZED PROTEIN COMPOSITION OBTAINED FROM AVIAN EGGSHELL MEMBRANE

(75) Inventors: Ronald E. Strohbehn, Nevada, IA (US); Lisa R. Etzel, St. Anthony, IA (US); Jesse Figgins, Ames, IA (US)

(73) Assignee: Biova, L.L.C., Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/906,287

(22) Filed: Oct. 18, 2010

(65) Prior Publication Data

US 2011/0033440 A1 Feb. 10, 2011

Related U.S. Application Data

(62) Division of application No. 12/253,719, filed on Oct. 17, 2008.

(60) Provisional application No. 60/980,607, filed on Oct. 17, 2007.

(51) Int. Cl.
*A61K 35/54* (2006.01)
*A61K 35/12* (2006.01)

(52) U.S. Cl. ........................... 424/581; 424/520

(58) Field of Classification Search .................. None
See application file for complete search history.

(56) References Cited

U.S. PATENT DOCUMENTS

| | | | |
|---|---|---|---|
| 5,132,399 | A | 7/1992 | MacDonald et al. |
| 6,946,551 | B2 | 9/2005 | Long et al. |
| 2004/0180025 | A1* | 9/2004 | Long et al. ............. 424/70.14 |
| 2007/0017447 | A1 | 1/2007 | Vlad |
| 2007/0172579 | A1 | 7/2007 | Blanton et al. |
| 2007/0178170 | A1 | 8/2007 | DeVore et al. |
| 2009/0104173 | A1* | 4/2009 | Strohbehn et al. ......... 424/94.61 |
| 2010/0029564 | A1* | 2/2010 | Strohbehn et al. ............ 514/12 |
| 2011/0020316 | A1* | 1/2011 | Minatelli et al. .......... 424/94.63 |

FOREIGN PATENT DOCUMENTS

| | | |
|---|---|---|
| JP | 5-97897 | 4/1993 |
| JP | 2004-229534 | 8/2004 |
| JP | 2004-229534 | 7/2005 |
| JP | 2006158354 | * 6/2006 |

OTHER PUBLICATIONS

Ahlborn, G. J. et al., "Identification of Eggshell Membrane Proteins and Purification of Ovotransferrin and Beta-NAGase from Hen Egg White", The Protein Journal, vol. 25, No. 1, Jan. 2006, pp. 71-81.
Arias, Jose L., et al. "Partial Biochemical and Immunochemical Characterization of Avian Eggshell Extracellular Matrices" Archives of Biochemistry and Biophysics, vol. 298, No. 1, Oct. 1992, pp. 293-302.
Cooke, A.S. et al., "Studies of Membrane, Mammilary Cores and Cuticle of the Hen Egg Shell", Br. Poult. Sci. II, pp. 345-352, 1970.
Kirschbaum, B. B. et al., "Glycoproteines Sulfates Des Membranes De L'Oeuf De Poule De Et L'Oviducte" Biophysica Acta, 320 (1973) 427-441.
Nakano, K. et al., "Sialic acid contents in chicken eggs and tissues", Canadian Journal of Animal Science, 1994, pp. 601-606.
Nakano, T., et al., "Chemical Composition of Chicken Eggshell and Shell Membranes", 2003 Poultry Science Association, Inc., pp. 510-514.
Wong, Mitchell et al., "Collagen in the Egg Shell Membranes of the Hen", Developmental Biology 104, pp. 28-36, 1984.
Yi, Feng et al., "Natural Bioactive Material: A Preparation of Soluble Eggshell Membrane Protein", Macromolecular Bioscience 2003, 3, pp. 234-237.
Yi, Feng et al., "Soluble eggshell membrane protein: preparation, characterization and biocompatibility" Biomaterials 25 (2004), pp. 4591-4599.
International Search Report, BIOVA, LLC, PCT/US2008/080336, Apr. 6, 2009, 2 pages.

* cited by examiner

*Primary Examiner* — Christopher R. Tate
(74) *Attorney, Agent, or Firm* — McKee, Voorhees & Sease, P.L.C.

(57) ABSTRACT

A solubilized protein composition is obtained from avian eggshell membrane without the use of proteolytic enzymes or cross-linking agents. The composition is essentially odor-free, has an ash content of less than 10% by weight of the composition and a protein content of at least 90% by weight of the composition including a mixture of solubilized proteins such as Type I collagen, Type V collagen, Type X collagen, elastin, lysozyme, ovotransferrin, desmosine, and/or B-N-acetylglucosaminidase, wherein the solubilized proteins are undenatured and retain biological activity.

18 Claims, 4 Drawing Sheets

SOLUBILIZED PROTEIN COMPOSITION OBTAINED FROM AVIAN EGGSHELL MEMBRANE

CROSS-REFERENCE TO RELATED APPLICATIONS

This application is a Divisional Application of Ser. No. 12/253,719 filed Oct. 17, 2008, which claims priority under 35 U.S.C. §119 of a provisional application Ser. No. 60/980,607 filed Oct. 17, 1997, which applications are hereby incorporated by reference in their entirety.

BACKGROUND OF THE INVENTION

Many industrial waste products such as pigskin, fish scale, and avian eggshell membranes are a source of valuable bioactive materials, including collagen, that have widespread applications in medical, health and cosmetic industries. To date, a major drawback to their use has been the difficulty in solubilizing these proteinaceous starting materials in a sufficiently stable and active pure form at an industrial scale so that high yield is achieved in an economic manner.

For example, solubilization of eggshell membranes has proven technically difficult. Recent processes to solubilize eggshell membranes include the use of mercaptopropionic acid, various extraction agents, or enzymes, such as peptidases, trypsin, and collagenases; however, problems have been associated with these procedures. The amount of protein solubilized from the starting material by these processes is low, the techniques are not cost-effective, and often the recovered protein components do not maintain their native activity. Therefore an inexpensive process for solubilizing eggshell membranes and other sources of proteinaceous materials while maintaining both yield, purity and activity of the solubilized protein is needed, particularly one suited for commercial scale implementation.

BRIEF SUMMARY OF THE INVENTION

The present invention relates to a process to provide for commercial-scale solubilization of various components from a proteinaceous material such as eggshell membranes. As a result of the present invention, one can produce a composition having large amounts of solubilized proteins from eggshell membranes. This process has an additional advantage in that the resulting composition may be used as a source for the isolation of other valuable components. Specific components, such as individual proteins, may be further purified from the composition thereby making it feasible to isolate proteins of interest from the composition.

The process for solubilizing proteinaceous material of the present invention includes subjecting the proteinaceous material to a sufficient amount of a basic solution for a sufficient length of time and temperature for hydrolysis to occur. The process also includes cooling the mixture of proteinaceous material/basic solution, and, if desired acidifying the mixture, to obtain solubilized proteins. This process may also include recovering the solubilized proteins from the mixture for use in various applications.

Therefore it is a primary object feature or advantage of the present invention to improve over the state of the art.

A further object, feature, or advantage of the invention is to provide a novel process for the solubilization of a proteinaceous material.

A further object, feature, or advantage of the invention is to provide a process for the solubilization of a proteinaceous material that produces solubilized protein that can be used in medical, cosmetic, pharmaceutic, dermatological or nutritional applications.

Another object, feature, or advantage of the invention is to provide a process for the solubilization of a proteinaceous material that substantially lowers the mineral (ash) content of the solubilized protein composition.

Yet another object, feature, or advantage of the invention is to provide a process for the solubilization of a proteinaceous material that increases the yield of the solubilized protein composition.

An object, feature, or advantage of the present invention is to provide a means to solubilize proteins from eggshell membranes.

It is a further object, feature, or advantage of the present invention is to provide a composition of solubilized proteins from eggshell membranes.

Yet another object, feature, or advantage of the invention is to provide a composition that is rich in proteins solubilized from eggshell membranes.

Still another object, feature, or advantage of the invention is to provide a cosmetic, medical, pharmaceutic, dermatological, or nutritional composition that is rich in proteins solubilized from eggshell membranes.

An object, feature, or advantage of the present invention is to provide a composition useful in treating an individual in need of proteins solubilized from eggshell membranes.

An additional object, feature, or advantage of the present invention is to provide a method of treating an individual in need of proteins solubilized from eggshell membranes.

A further object, feature, or advantage of the present invention is to provide a process for preparing a composition that has solubilized proteins obtained from an eggshell membrane.

A still further object, feature, or advantage of the present invention is to provide a process which is suitable for implementation on a commercial/industrial scale.

One or more of these and/or other objects, features, or advantages of the present invention will become apparent from the specification and claims that follow. No single embodiment of the invention need fulfill all or any of the objects stated herein.

DETAILED DESCRIPTION OF THE PREFERRED EMBODIMENT

Figure 1:
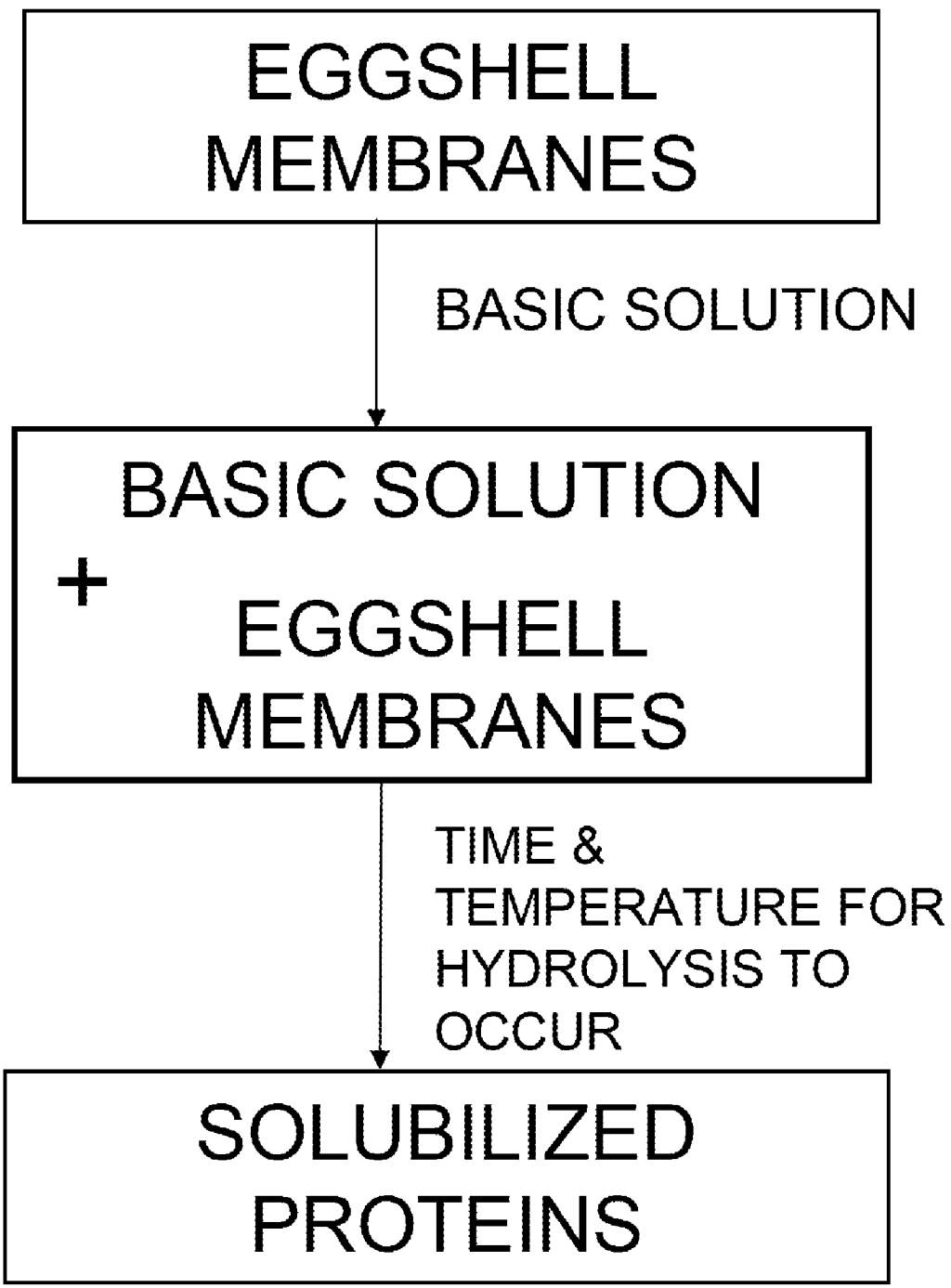
FIG. 1 is a flow chart for one embodiment of a process for solubilizing eggshell membranes.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, processes and examples are illustrative only and not limiting. The following is presented by way of illustration and is not intended to limit the scope of the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims.

To date, a composition containing proteins solubilized from eggshell membrane has not been obtainable on a commercial scale due to lengthy procedures, low yield of proteins and polysaccharides, or lack of bioactivity of isolated proteins. There is no known process for the preparation of a composition from eggshell membrane that overcomes current technical difficulties and produces a high yield, solubilized protein composition which is highly pure and undenaturated. The solubilized composition obtained by the process of the present invention has surprising levels of proteins, polysaccharides, and amino acids, is essentially free of odor, and can be efficiently prepared. Advantageously, since proteolytic enzymes or cross-linking agents are not used, processes of the present invention are also more economic than those of current practices.

The process of the invention is suited for solubilization of protein from various proteinaceous materials. Any suitable proteinaceous material may be employed in the practice of the present invention. As used herein, the term "proteinaceous material" is used to describe a material comprising proteins, polypeptides or peptides. Proteinaceous materials may be obtained and prepared from any number of resources. Examples include but are not limited to connective tissues, such as the combs of roosters, avian eggshell membranes, skin, fishscale, flesh, or cartilage. As used herein, the term "eggshell membrane" refers to any part of the eggshell membrane, for example, the inner eggshell membrane, the outer eggshell membrane or both. The eggshell membrane also includes the eggshell membrane in its various forms, for example, frozen, raw (wet) or dried.

Avian eggshell membranes are conventionally considered a waste product due in part to both the difficulties encountered in separating the eggshell membrane from the eggshell and further in the difficulties in processing the eggshell membrane in a manner that will result in obtaining proteins, polypeptides or peptides of interest. Various measures of the protein content of eggshell membranes are present in the prior art.

Examples of one measure of the amount of protein and individual amino acids known to be found in egg shell membranes are shown below from U.S. Pat. No. 6,899,294 to MacNeil.

| Protein And Individual Amino Acids in Eggshell Membranes | % |
|---|---|
| Protein | 85 |
| Lysine | 3.35 |
| Histidine | 3.48 |
| Arginine | 6.46 |
| Threonine | 4.60 |
| Glutamic Acid | 9.70 |
| Proline | 9.34 |
| Glysine | 4.94 |
| Cysteine | 8.50 |
| Valine | 6.30 |
| Methionine | 3.09 |
| Isoleucine | 3.19 |
| Leucine | 4.30 |
| Tyrosine | 1.73 |
| Phenylalanine | 1.65 |

Another measure of the typical amino acid composition of egg shell membranes is provided by U.S. patent application Ser. No. 10/797,747, published patent application no. 20040180025 (Long et al.) and is set forth in the below table:

| Typical Amino Acid Composition of Eggshell Membrane Protein | % |
|---|---|
| Lysine | 2.88 |
| Tryptophan | 2.51 |
| Leucine | 3.85 |
| Aspartic Acid | 7.01 |
| Proline | 8.23 |
| Isoleucine | 2.01 |
| Threonine | 4.42 |
| Glycine | 3.99 |
| Histidine | 2.79 |
| Arginine | 5.33 |
| Tyrosine | 1.33 |
| Glutamic Acid | 8.23 |
| Cystine | 6.01 |
| Alanine | 2.00 |
| Methionine | 2.85 |
| Valine | 5.13 |
| Phenylalanine | 1.48 |
| Serine | 4.28 |

Another measure of the constituents of egg shell membranes (in percentage) is provided by Long et al and is set forth in the below table:

| Typical Constituents of Eggshell Membrane | % |
|---|---|
| Collagen | 35 |
| Glucosamine | 10 |
| Chondroitin | 9 |
| Hyaluronic acid | 5-10 |

Prior testing on avian egg shell membranes with a particular process is described in U.S. patent application Ser. No. 11/471,766, published patent application no. 20070017447 entitled Avian Eggshell Membrane Polypeptide Extraction Via Fermentation Process. That testing resulted in the following composition:

| Constituent | % |
|---|---|
| Protein | 90.08 |
| Aspartic Acid | 7.98 |
| Threonine | 5.19 |
| Serine | 5.05 |
| Glutamic Acid | 11.91 |
| Proline | 10.79 |
| Glycine | 5.43 |
| Alanine | 2.46 |
| Valine | 6.02 |
| Isoleucine | 2.91 |
| Leucine | 4.19 |
| Tyrosine | 1.57 |
| Phenylalanine | 1.60 |
| Lysine | 3.21 |
| Histidine | 3.38 |
| Arginine | 6.89 |
| Cystine | 6.72 |
| Methionine | 3.50 |
| Tryptophan | 3.64 |

Thus, there are numerous types of proteins, polypeptides, and peptides in eggshell membranes that can be extracted provided that the membranes can be solubilized. The eggshell membrane may be obtained from any number of resources, including an egg-breaking facility. The eggshell membrane may be separated from the egg white and eggshell using any suitable technique, for example mechanical or chemical methods or a combination of methods. For example, unseparated eggshells may be processed as described in U.S. patent application Ser. No. 11/333,697, published application no. 20060159816, herein incorporated by reference in its entirety. The eggshell membrane separation method includes placing the unseparated eggshells in a fluid tank containing a fluid mixture, such as a mixture of distilled water and acetic acid, and applying cavitation to thereby assist in separating the eggshell membranes from the eggshells. The eggshell membranes may then be recovered using any suitable technique, preferably the separation process does not damage or denature the proteins. The isolated eggshell membrane may be processed as described herein. For example, the eggshell membranes may be subjected to a solubilization process for solubilizing at least one type of polypeptide or polysaccharide from the eggshell membranes. Components of interest that may be solubilized include but are not limited to collagen, elastin, desmosine, lysozyme, glucosamine, chondroitin, ovotransferrin, B-N-acetylglucosaminidase, hyaluronic acid, amino acids or other components of interest. The collagen may be Type I collagen, Type V collagen, Type X collagen or combinations thereof. The components may be solubilized from the eggshell membrane and purified for numerous uses.

As shown in FIG. 1, in one embodiment, the process of the present invention includes subjecting a proteinaceous material such as eggshell membrane to a sufficient amount of a basic solution so that hydrolysis of the eggshell membrane occurs. The basic solution is added to the eggshell membrane to produce a supernatant having a basic pH. As used herein, the term basic refers to a pH greater than 7. The pH of the supernatant may be adjusted to a pH of from about 9.0 to a pH of from about 11.5, preferably from a pH range of from about 10.5 to about 11.5. Any suitable basic solution may be used including but not limited to sodium hydroxide, potassium hydroxide, and calcium hydroxide. The sufficient amount of basic solution to add to the proteinaceous material may be determined in any number of ways as appreciated by those skilled in the art. For example, the sufficient amount of the basic solution necessary to achieve a pH from about 9.0 to about 11.5 may be determined based on the total weight of the proteinaceous material, preferably based on the solid (dry) weight of the proteinaceous material, and the molarity of the basic solution. It is preferred that the temperature and pH be closely monitored, so that functional proteins, polypeptides and peptides are obtained rather than mostly amino acids. As used herein, a "polypeptide", "peptide" or "protein" are used interchangeably. In one aspect, the process includes exposing the supernatant to the basic solution for a sufficient length of time and temperature for hydrolysis to occur. One skilled in the art will appreciate that the time needed for the hydrolysis reaction of the proteinaceous material to proceed will vary in part based on the temperature selected. Accordingly, hydrolysis of the proteinaceous material may be carried out at any suitable temperature for any suitable length of time, for example, the temperature may be from a range of about 30° C. to about 65° C., preferably from a temperature of about 45° C. to about 60° C., and more preferably from a temperature of at least about 50° C. The hydrolysis time can be as long as necessary to achieve the desired result. The length of time the proteinaceous material is subjected to hydrolysis may vary from as little as hours, such as 3 to 24 hours, to days depending on the temperature and other conditions used. For example, use of a higher temperature, for example of 50° C. compared to 30° C., and stirring the mixture of proteinaceous material/basic solution would reduce the length of time needed for hydrolysis reaction to occur. One skilled in the art can monitor the progress of the hydrolysis reaction using standard techniques such as trichloroacetic acid (TCA) protein precipitation and/or visualization methods. For example, one could take a sample of the supernatant, precipitate proteins out using TCA, and analyze the supernatant after TCA precipitation for levels of nitrogen (indicative of free amino acids). Alternately, hydrolysis may be monitored by using simple visualization methods over selected time intervals. Typically, measurements are performed about three hours after subjecting the proteinaceous material to the basic solution to assess hydrolysis of the proteinaceous material into soluble proteins. A sample may be taken from the proteinaceous material/basic solution mixture and the sample analyzed for the presence of insoluble proteins of the eggshell membrane. Samples are spun down using centrifugation and the contents visually analyzed for the presence of a yellow material of non-hydrolyzed eggshell membranes, i.e. insoluble eggshell membrane proteins. It is noted that spun down samples may also contain eggshell particulates which are white in color. If the yellow material of insoluble eggshell membrane proteins is observed then the hydrolysis reaction is allowed to proceed and samples from the mixture are taken at 15 to 20 minute intervals thereafter and evaluated. Typically, the reaction is allowed to proceed until the yellow insoluble proteins are no longer present in the spun down samples. Thus, one skilled in the art can determine whether the proteinaceous material has been substantially hydrolyzed, whether more time is needed or whether the reaction has proceeded too long as indicated by the hydrolysis of the proteins into amino acids.

In one aspect, the process of the invention includes cooling the supernatant. For example, the temperature of the supernatant comprising the hydrolyzed proteinaceous material may be adjusted to a temperature of from about 2° C. to about 18° C., more preferably to a temperature of about 2° C. to about 7° C.

In another aspect, the process includes the removal of particulates, such as eggshells or fine calcium from eggshells, from the supernatant containing the hydrolyzed proteinaceous material by any suitable separation technique. This may be accomplished in any number of ways, including, but not limited to centrifugation, ultra-centrifugation, filtration or microfiltration, or combinations of separation techniques. For example, centrifugation may be used to separate particulates from the supernatant containing the hydrolyzed proteinaceous material and the supernatant removed by decanting, pumping, and the like. Any number of filtration techniques may be used for the process of the present invention, including but not limited to gravity filtration, pressure filtration, vacuum filtration, batch filtration, membrane filtration, filter press, continuous filtration, or any suitable combination. Filtration may include the use of any suitable filter that is capable of removing particulates from the supernatant. A suitable filter may include but is not limited to a drum filter, a disk filter, filter press or a sock filter. Preferably, a filter sock with a 100 micron to 865 micron sock size is used. The filter may be made from a variety of materials such as, but not limited to, sintered-metal, cloth, polymeric fiber, natural fiber, paper such as a coffee filter, metal mesh, pulp, ceramic, or a combination of the foregoing materials, and the like. The pore size of the filter may be of any size so long as it filters out the desired particulates. The range of pore size may be from of 0.01 micrometers to 100-200 micrometers, or greater.

The resulting solubilized components in the supernatant can be further purified, isolated, and/or concentrated. For example, in one aspect, the process of the present invention includes removing salt (ash) or minerals from the supernatant. The relative amount of salts/minerals in the supernatant can be determined using any suitable technique including measuring the conductivity of the supernatant, using, for example, a meter to measure conductivity in milliSiemens (mS), ppm, ampre/volts, etc. The level of salt in the supernatant can be adjusted so that the final solubilized composition has the desired or acceptable level or percentage of ash, depending on the intended use for the resulting solubilized composition and the industry standards.

For example, with respect to the solubilization of avian eggshell membranes, a conductivity of a supernatant that is at or above 5 milliSiemens/cm may be considered to be a high level of salt/mineral. If the salt/mineral content in the supernatant is not reduced, it will become ash in the resulting solubilized composition. Ash is undesirable because it is potentially perceived as a "filler" in the consumed product. Additionally, many health conscious consumers may desire to limit their consumption of salt. The reduction in the amount of ash in the supernatant increases the percentage of protein content in the recovered solubilized composition.

If the supernatant has a conductivity that would result in the solubilized protein composition having an ash content that is unacceptable, salts/minerals may be removed from the supernatant until an acceptable level of salt is present in the supernatant. In some cases, a supernatant having less than 5 milliSiemens/cm (mS/cm) is acceptable, preferably 4 or less mS/cm, more preferably from about 2 to about 4 mS/cm.

The salt/minerals may be removed from the supernatant using any suitable process, for example, filtration, dialysis or ion exchange. The process may include separating the hydrolyzed proteins in the supernatant from salt and if desired, specific molecules, using a membrane. The separation may be performed using any suitable technique, such as the use of a membrane. This also allows for the concentration of a composition that has high levels of solubilized proteins. The composition may also contain polysaccharides. Any process that allows for concentration may be used, although, preferably the concentration process maintains the biological activities of the composition or of the individual components in the composition. Typically, the supernatants are passed through a membrane having the desired nominal molecular weight cut-off value, leaving solubilized proteins and other solubilized components having a molecular weight larger than the cut-off value behind. In one embodiment, a membrane with a nominal molecular weight cut-off value of about 1000-3000 Daltons is used, resulting in a composition that has high amounts of solubilized proteins, but allowing amino acids and other small molecules to pass through. If desired, the amino acids may be recovered from the supernatant for use in any number of applications, such as consumable products. If desired, a specific component or a mixture of specific components in the solubilized composition may be isolated. Solubilized components may be isolated in any manner that is convenient. As appreciated by those ordinarily skilled in the art, the selection of membrane size can be used to obtain a composition enriched for a particular size of protein or population of proteins. For example, use of a membrane having a nominal molecular weight cut-off value of about 100 kDa may be used to isolate elastin and other solubilized proteins larger than 100 kDa and proteins that are less than 100 kDa such as collagen and desmosine. Desmosine, an anti-oxidant of three amino acid residues of lysine, may be released when the elastin is solubilized, and if desired, may be further concentrated using a membrane having a nominal molecular weight cut-off value of less than 500 molecular wt.

Advantageously, filtering and/or performing dialysis of the supernatant may remove sulfur compounds from the supernatant, thereby reducing the sulfur odor of the supernatant. In another aspect, the process of the invention may include removing odor causing components from the supernatant, for example, by using a filter with an odor-absorbing compound such as a charcoal filter or an activated carbon filter. Additionally, an odor-reacting compound that is an oxidizing agent, such as hydrogen peroxide, may be added to the supernatant to reduce sulfur odors. The process may also include reducing the number of microorganisms in the supernatant by subjecting the supernatant to filtration, for example, a 0.8 micrometer filter.

In another aspect, the process includes adjusting the pH of the supernatant or permeate comprising the hydrolyzed proteins so that the supernatant or permeate has a pH from about 6.0 to about 8.0, preferably to a pH of about 7.0. The pH may be adjusted using any suitable acidic solution that has a pH of less than 7, including but not limited to a solution of acetic, oxalic, phosphoric, chloroacetic, citric, formic, benzoic, oxalic, succinic, acetic, propionic hydrochloric, nitric, sulfuric, hydrotropic, hydrologic, perchloric, chloric, phosphoric, or sulfurous acid or combinations thereof. In one embodiment, the pH and the temperature of the supernatant or permeate are lowered simultaneously or consecutively, although it is preferred that the supernatant be cooled prior to addition of the acidic solution.

In a preferred embodiment, the removal of salts, for example, by dialysis, pH adjustment of the supernatant or permeate from a basic pH to a pH of about 7.0, and removal of sulfur odor using hydrogen peroxide are performed simultaneously. As appreciated by one skilled in the art, these steps may be performed consecutively, in a different order, or omitted and still yield a composition of solubilized proteins.

The solubilized composition resulting from the process of the present invention may be prepared in any number of forms or formulations. In one embodiment, the composition of solubilized protein is prepared as a protein powder using any suitable technique, including but not limited to lyophilization, vacuum drying, freeze drying, spray drying, drum drying, paddle-drying, super critical fluid processing, air drying, or other forms of evaporative drying. The drying step may be carried out any suitable temperature, for example, with respect to freeze drying, a preferred temperature range is from about 23° C. to about 40° C., with 27° C. being the more preferred temperature.

The present invention is advantageous in that multiple components are efficiently and economically solubilized from the eggshell membrane at the same time. Additionally, if desired, one or more specific components may be isolated from the solubilized eggshell membrane, such as elastin, collagen or desmosine. Thus, the present invention allows for the production of a composition of a specific component or combination of selected components in amounts suitable for use in a particular application. Thus, the composition may be customized for use in a particular product, for example, a cosmetic product or a dietary supplement. Advantageously, the compositions of the present invention are essentially odor-free.

Once the proteinaceous material or source is solubilized, one skilled in the art would be able to readily use standard biochemistry techniques such as membrane filtration or chromatography to isolate a protein of interest. Accordingly, the process of the invention may also include isolating from the supernatant or dried solubilized composition various proteins and polysaccharides of interest depending on the source of the starting proteinaceous material. For example, proteins of interest that may be isolated from solubilized avian eggshell membrane include but are not limited to elastin, desmosine, lysozyme, ovotransferrin, B-N-acetylglucosaminidase, collagen such as Type I collagen, Type V collagen, Type X collagen, or combinations thereof or other products of interest. Polysaccharides of interest that may be isolated include but are not limited to hyaluronic acid, glucosamine, and chondroitin.

Figure 2:
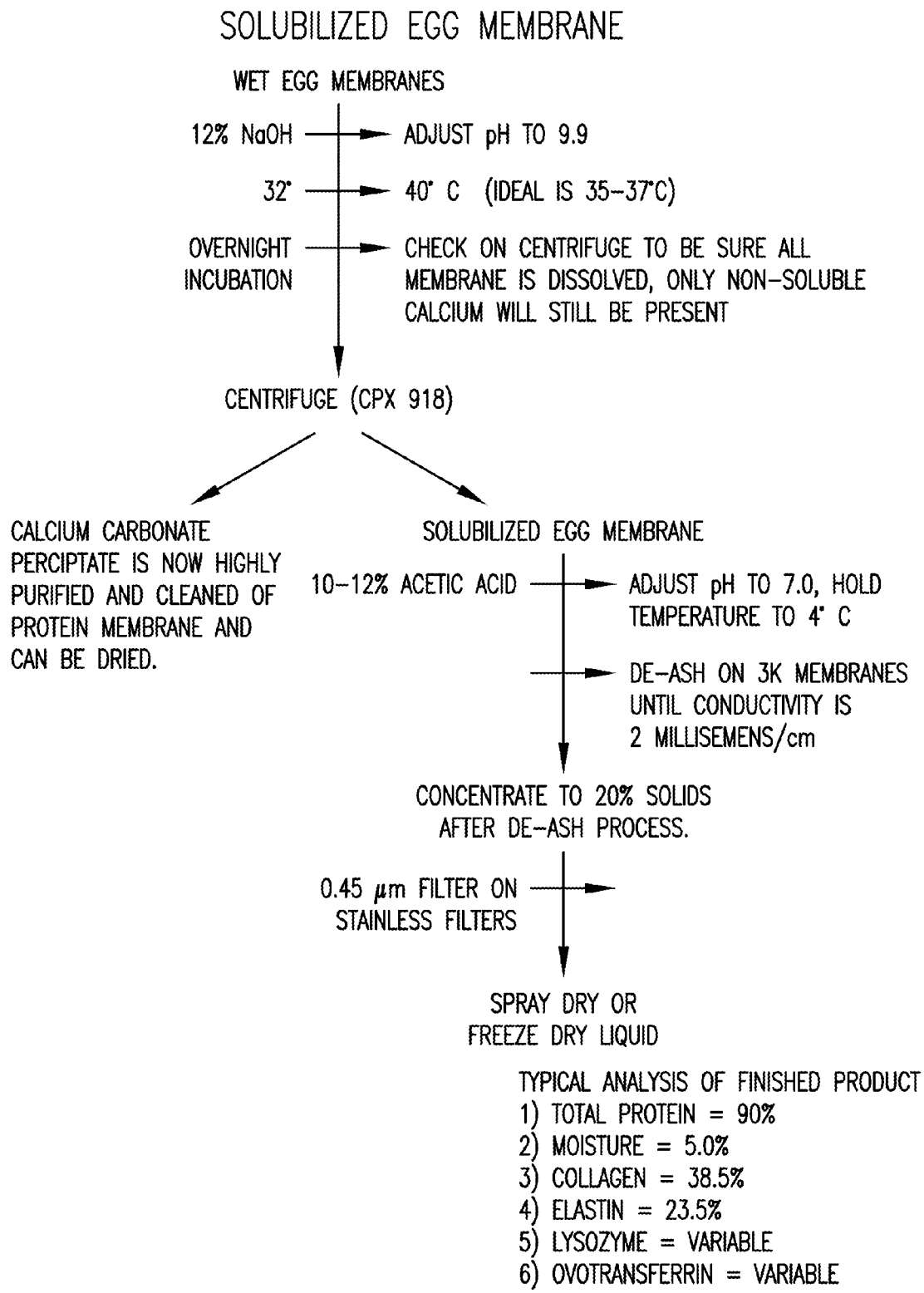
FIG. 2 is a flow chart for one embodiment of a process for solubilizing eggshell membranes.

In one embodiment, a soluble protein composition may be obtained from methods of the present invention. In one aspect, the protein composition may include elastin, glucosamine, chondroitin, desmosine, ovotransferrin, B-N-acetylglucosaminidase, collagen such as Type I collagen, Type V collagen, and/or Type X collagen, amino acids or combinations thereof. The amino acids present in the composition may include tryptophan, cystine, methionine, aspartic acid, threonine, serine, glutamic acid, proline, glutamic acid, proline, glycine, alanine, valine, isoleucine, tyrosine, phenylalanine, lysine, histidine, arginine, hydroxyproline and the like. The composition may also include hyaluronic acid, glucosamine, and chondroitin. In one aspect, the composition is more than 50%, 55%, 60%, 65%, 70%, 75%, 80%, 85%, 90% or 95% protein per weight of composition. In one aspect, the composition includes at least 10%, 15%, 20%, 25%, 30%, 35%, 40%, 45%, 50%, 55%, 60%, 65%, 70%, 75% or 80% collagen and/or least 1% elastin. Of the collagen present, the collagen may be 5%, 10%, 15%, 20%, 25%, 30%, 35%, 40%, 45%, 50%, 55%, 60%, 65%, 70%, 75%, 80%, 85%, 90% or 95% of Type I collagen. The composition may include 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% of Type V collagen. The collagen of the composition may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% of Type X collagen. The amount of elastin in the composition may vary depending on the size of membrane used to isolate the solubilized proteins. As shown in FIGS. 2 and 3, the composition may contain at least 10%, 15%, 20%, 25%, 30%, 35% or even 40% elastin. In one embodiment, the invention includes an isolated, soluble protein composition that is at least 10%, 15%, 20%, 25%, 30%, 35%, 40%, 45%, 50%, 55%, 60%, 65%, 70%, 75%, 80%, 85%, 90%, 95%, 96%, 97%, 98% or 99% soluble. The composition or protein is "soluble" or "solubilized" if at least at least 10% (by weight) of the protein or composition dissolves or does not aggregate in distilled water. Preferably, solubility of the protein or composition is assessed in distilled water, for example, at a concentration of 1 gram of the protein or composition per 9 grams of distilled water.

The failure to develop a commercially feasible process of solubilizing various components from eggshell membrane is due in part to failure by others to demonstrate high yields of a product in a highly purified, soluble form and that has retained bioactivity. As used interchangeably herein, a "bioactivity", "biological activity" or "native activity", refers to a function exerted by an intact, non-dentatured protein, polypeptide or peptide as determined in vivo, or in vitro, according to standard techniques. As described herein, the compositions of the present invention may be obtained from eggshell membranes without the use of proteolytic enzymes or cross-linking agents. Accordingly, the solubilized protein compositions are believed to be substantially pure, undenatured and retain biological activity.

Accordingly, a method of the present invention includes treating an animal or human in need of a component solubilized from eggshell membrane, e.g. protein, peptides, or amino acids, by administering a composition of the present invention. The invention also provides a method of treating a variety of diseases, disorders, and conditions that benefit from an effective amount of one or more components obtained from solubilized eggshell membrane. As used herein, unless otherwise defined in conjunction with specific diseases or disorders, the term "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. Accordingly, the composition or components, e.g. proteins, isolated thereof may be used in any number of applications, including but not limited to products or services in the cosmetic industry, see, for example, U.S. Pat. No. 7,169,379 to Kouzuki; products in the health industry, for example, products for use in joint health; and products in the medical industry, such as for wound healing, see U.S. Pat. No. 7,041,868 to Greene. Such applications are known in the art as well as the appropriate techniques for inclusion in such applications.

Accordingly, the present invention also relates to any pharmaceutical, dermatological, medical, nutritional or cosmetic compositions comprising a component obtained from eggshell membrane using a process of the present invention. The composition may include an effective amount of at least one or more components obtained from solubilized eggshell membrane. As the diseases, disorders or conditions that would benefit from these compositions are well known, the compositions may be designed such that they contain appropriate levels effective for treatment of the particular disease, disorder or condition. The compositions may generally be used in any formulation that is effective for treatment and the intended mode of administration. For example, compositions of elastin or collagen such as Type I collagen, Type V collagen, and/or Type X collagen, for use in dermatological or cosmetic treatments may be formulated in topical or injectable forms and the like. Compositions comprising solubilized proteins for use in nutritional or medical applications may be formulated in any suitable form, e.g. aqueous or dried, and administered by any effective route, such as orally or intramuscularly. As appreciated by one skilled in the art, compositions of the present invention can be administered in a variety of ways including oral, enteral, parenteral, topical, sublingual, by inhalation spray, rectal and other appropriate routes of administration, such as oral, subcutaneous, transdermal, transmucosal, iontophoretic, intravenous, intramuscular, intraperitoneal, intranasal, subdural, rectal, and the like.

Compositions containing solubilized components from eggshell membranes of the present invention may be in any form suitable for the intended mode of administration, including, for example, a powder, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compositions of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of emulsions, creams, ointments, transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE

The present invention is further defined in the following Examples, in which parts and percentages are by weight and degrees are Celsius, unless otherwise stated. The disclosure of each reference set forth herein is incorporated herein by reference in its entirety.

Example 1

Shown below is data resulting from the analysis of various samples of the resulting protein composition obtained by solubilizing avian eggshell membrane using a process of the present invention.

As indicated below, the solubilized protein composition was spray dried (SD), freeze dried (FD), or paddle dried (PD). Paddle dried is a common technique used by some egg breaking facilities to dry eggshells on a commercial scale.

The total protein (TP) concentration of the solubilized protein composition was measured using Leco instruments (St Joseph, Mich.) following the Association of Analytical Chemists (AOAC) protein by combustion method 990.03. The solubilized protein composition was determined "as is" in its current physical state as well as on a "dry basis".

The ash content was determined using AOAC method 942.05. The percent solubility of the resulting protein composition was determined using standard techniques. The percent collagen, elastin and sulfated glycans were determined using various commercially available assays, for example, colorimetric kits such as Sircol, Fastin, Blyscan assays (Biocolors Ltd, Northern Ireland). Percent hyaluronic acid was determined by measuring uronic acid by a carbazole method. The amino acid profile was performed by Eurofins Scientific, Inc. (Des Moines, Iowa). A Standard Plate Count (SPC) procedure was used to determine the presence of bacteria in each of the samples, as indicated below by SPC.

The measurement of color was determined using the Hunter L, a, b standard color scale, which is described below. Hunter L, a, b values are standard color scale values that indicate differences in brightness, hue and saturation using a standard color system which relates lightness as L values, and hue and croma as a combination of a and b values on a coordinate scale, where a represents redness-greenness and b represents yellowness-blueness. L values describe the degree of darkness, where a value of 100 equals white and that of 0 equals black. a-values describe the degree of redness, which increases with an increasing a-value. b-values describe the degree of yellowness, which increases with increasing b-value. L, a, b and opacity theory and measurement are further described in the Hunter Lab Instruction Manual Hunter. L, a, b and color scale values and opacity may be measured using a colorimeter available from Hunter Associate Laboratory, Inc. of Reston, Va., U.S.A. or the Color Machine Model 8900 available from Pacific Scientific.

As shown in FIG. 2, wet, dry or frozen membranes were put into a stainless (316) tank and 12% NaOH was added and the mixture was incubated at 32-40° C. overnight. After hydrolysis the mixture was cooled to 38-45° F. to slow continued hydrolysis. The mixture was centrifuged to separate eggshells from solubilized proteins. The centrifuged solubilized proteins were then dialyzed through 3,000 MWCO membranes until ash was reduced to a conductivity reading of 2-4 mS/cm. The proteins were then pH adjusted with 12% acetic acid to a pH of 6.8-8. The pH adjusted protein mixture was then concentrated to a solids content of 25% to 30% at which time it could be spray dried or freeze dried. Tables 1 and 2 below show the percent analysis of samples from the resulting composition.

TABLE 1

Percent analysis of sample compositions.

| Sample | Type (SD, FD, PD) | Leco TP % as-is | Leco TP % dry basis | Ash % as-is | Ash % dry basis | Moist % | Solids % | Solubility % | Collagen % |
|---|---|---|---|---|---|---|---|---|---|
| 1 | FD | 90.45 | 94.50 | 6.67 | 6.97 | 4.29 | 95.71 | 95.40 | 16.96 |
| 2 | FD | 91.56 | 95.64 | 6.96 | 7.27 | 4.27 | 95.73 | 92.26 | 18.49 |
| 3 | FD | 90.25 | 92.61 | 7.35 | 7.54 | 2.55 | 97.45 | 99.70 | 17.62 |
| 4 | SD | 91.66 | 100.03 | 6.22 | 6.79 | 8.37 | 91.63 | 98.16 | 15.44 |

TABLE 2

Percent analysis of sample compositions.

| Sample | Hyaluronic Acid % | Elastin % | Sulfated Glycans % | SPC's (cfu's/g) | Salmonella (neg/25 g) | Color (L) | Color (a) | Color (b) |
|---|---|---|---|---|---|---|---|---|
| 1 | 0.13 | 29.52 | ND | <100 | neg | 63.41 | 2.41 | 18.88 |
| 2 | 0.17 | 24.20 | ND | <100 | neg | 63.78 | 3.35 | 20.64 |
| 3 | 0.15 | 22.50 | 0.01 | 1,800 | neg | 57.47 | 0.57 | 15.42 |
| 4 | 0.20 | 24.52 | ND | <1,000 | neg | 86.37 | −0.48 | 11.08 |

As shown in FIG. 3, various soluble protein compositions may be obtained using various membrane sizes in accordance with the methods of the present invention. A typical test analysis of the compositions obtained from processing 600 pounds of eggshell membranes using various sized membranes are shown in Tables 3-6.

Example 2

Figure 3A:
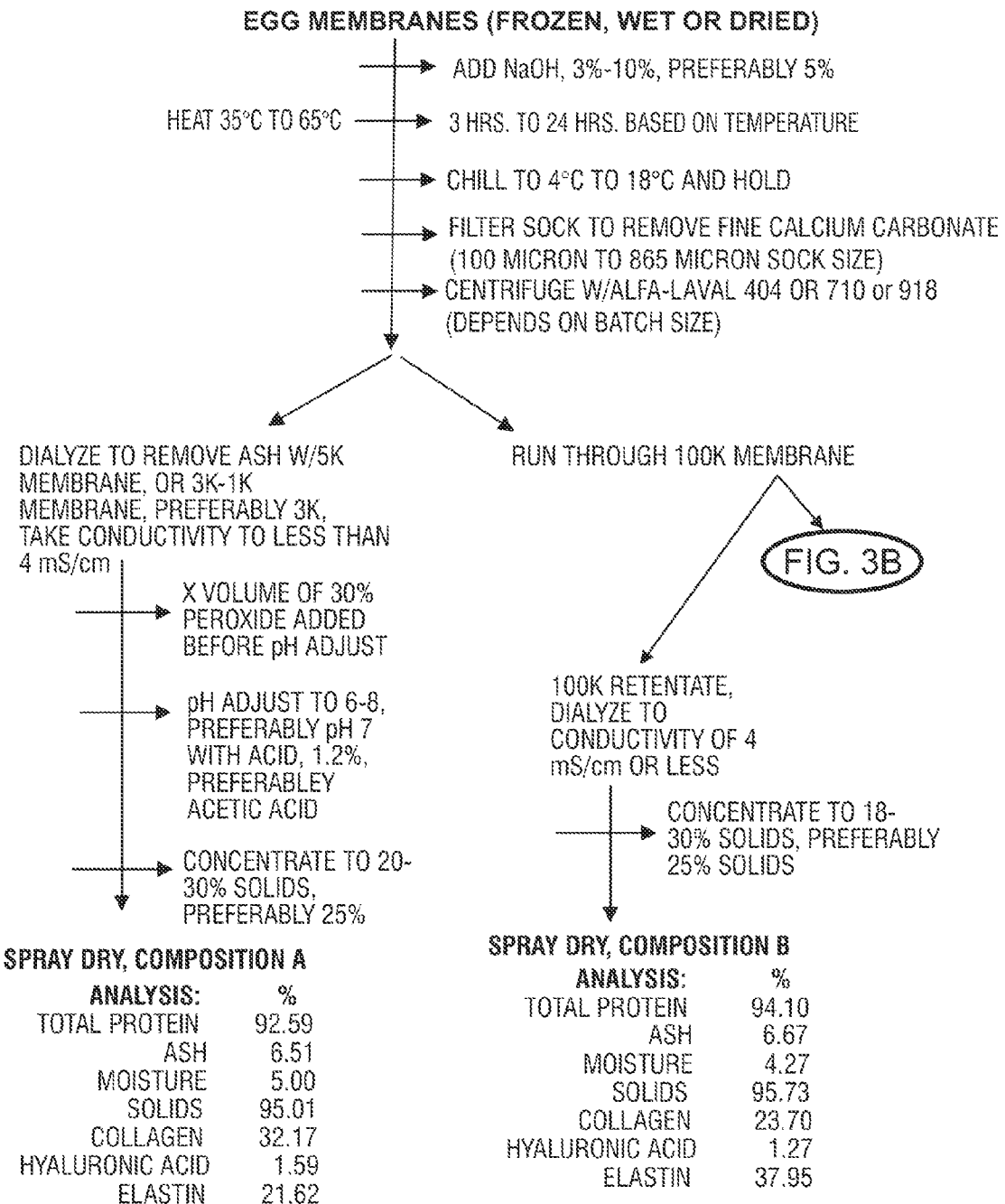
FIGS. 3A and 3B are flow charts for one embodiment of a process for solubilizing eggshell membranes.

Process for Making the Product Referred to as Composition a in FIG. 3A

The process for making the product referred to as Composition A includes adding eggshell membranes (wet, dry or frozen) to a jacketed 316 stainless tank followed by 5% sodium hydroxide. The tank contents were heated to 50° C. while stirring until hydrolysis was completed which is 3 to 4 hours. The tank stirrer was shut off after hydrolysis was complete and eggshell is allowed to settle out. (Approx. 30 min.) Hydrolysis was monitored until no membrane was visible and only the eggshell remains.

The hydrolyzed membrane was pumped through a 250-500 μm membrane and into the centrifuge for separation of eggshell fines from the supernatant liquid.

After centrifuging, the supernatant liquid was pumped into a 1,000 Dalton to 10,000 Dalton membrane system, where the ash was removed until it measures less than 4 milliSiemens/cm at which time the pH was adjusted to pH 6.8-7.6 with 0.5% acetic acid and dialyzed with one more volume of water. The dialyzed, pH adjusted supernatant was concentrated to 20-30% solids and then spray dried in a nozzle dryer to generate Composition A. FIG. 3A and Table 3 below shows the resulting composition.

TABLE 3

Percent analysis of components of Composition A.

| Composition A Analysis | % |
|---|---|
| Total protein | 92.59 |
| Ash | 6.51 |
| Moisture | 5.00 |
| Solids | 95.01 |
| Collagen | 32.17 |
| Hyaluronic Acid | 1.59 |
| Elastin | 21.62 |

Further analytical results indicate that the following amino acids are present in the following Composition A:

TABLE 4

Percent analysis of amino acid present in the Composition A.

| Amino Acid | (%) |
|---|---|
| Tryptophan | 3.53 |
| Cystine | 2.47 |
| Methionine | 3.79 |
| Aspartic Acid | 8.33 |
| Threonine | 3.08 |
| Serine | 3.30 |
| Glutamic Acid | 14.61 |
| Proline | 9.85 |
| Glycine | 4.38 |
| Alanine | 2.25 |
| Valine | 7.51 |
| Isoleucine | 3.47 |
| Leucine | 4.72 |
| Tyrosine | 1.72 |
| Phenylalanine | 1.57 |
| Total Lysine | 5.99 |
| Histidine | 3.23 |
| Arginine | 6.58 |
| Hydroxyproline | 0.22 |

Example 3

Process for Making the Product Referred to as Composition B in FIG. 3A

Egg membranes (wet, dry or frozen) were added to a jacketed 316 stainless tank followed by 5% sodium hydroxide. The tank contents were heated to 50° C. while stirring until hydrolysis was completed which is 3 to 4 hours. The tank stirrer was shut off after hydrolysis was complete and eggshell is allowed to settle out. (Approx. 30 min.) Hydrolysis was monitored until no membrane is visible and only the eggshell remains.

The hydrolyzed membrane is pumped through a 250-500 μm membrane and into the centrifuge for separation of eggshell fines from the supernatant liquid.

After centrifuging, the hydrolyzed membrane was diafiltered through a 100,000 molecular weight cutoff membrane. The retentate was saved and conductivity was reduced from 140 milliSiemens/cm to 4 milliSiemens/cm and concentrated to 25-30% solids and spray dried. The results are shown in the following table and in FIG. 3A.

TABLE 5

Percent analysis of components of the Composition B composition.

| Composition B Analysis | % |
| --- | --- |
| Total protein | 94.10 |
| Ash | 6.67 |
| Moisture | 4.27 |
| Solids | 95.73 |
| Collagen | 23.70 |
| Hyaluronic Acid | 1.27 |
| Elastin | 37.95 |

Example 4

Figure 3B:
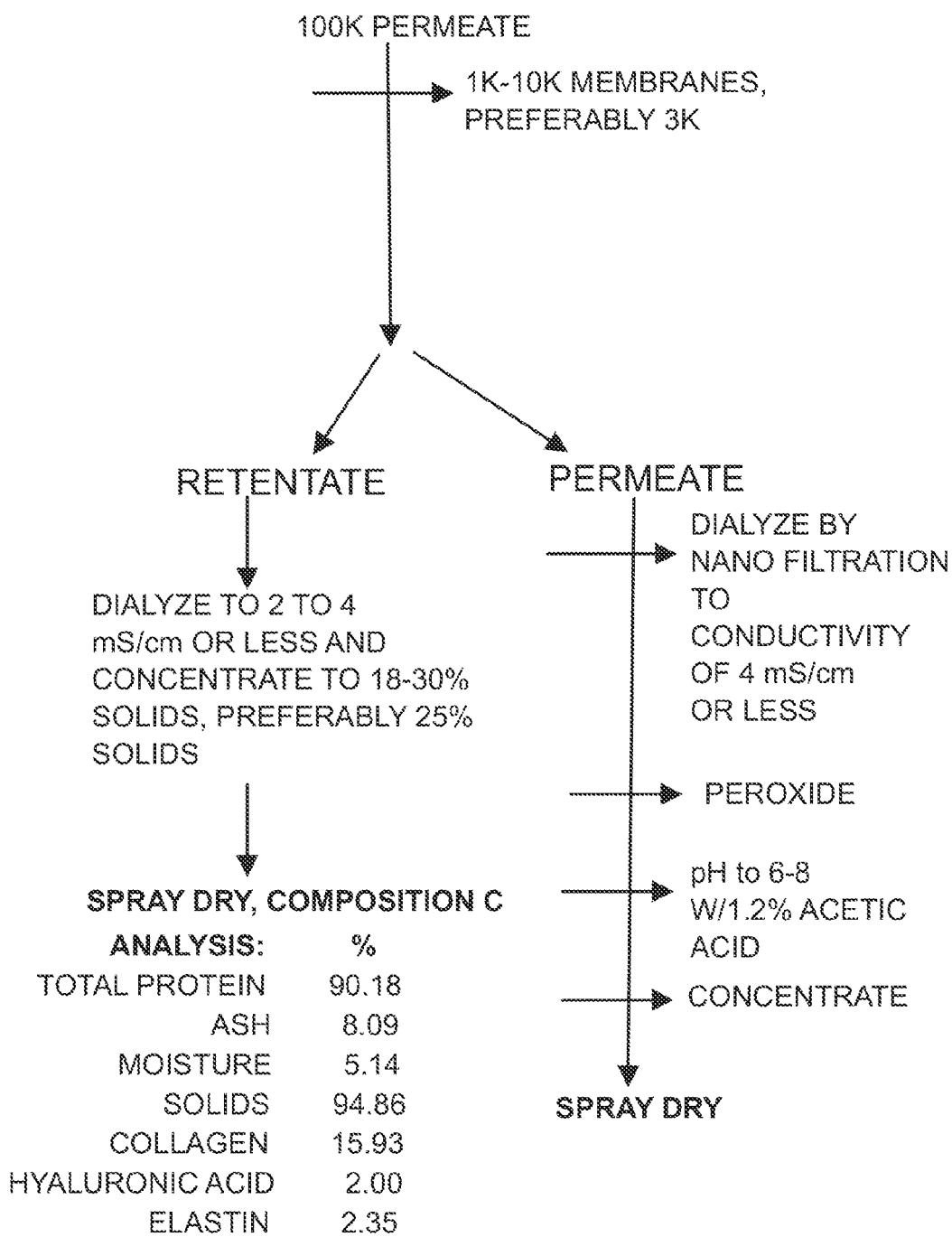

Process for Making the Product Referred to as Composition C in FIG. 3B

The permeate was collected from the 100,000 molecular weight cutoff membranes and dialyzed with 10,000 molecular weight membranes. Conductivity was reduced from 140 milliSiemens/cm to 4 milliSiemens/cm and concentrated to 25-30% solids and spray dried. The resulting composition is provided in FIG. 3B and Table 6 below.

TABLE 6

Percent analysis of components of the Composition C composition.

| Composition C Analysis | % |
| --- | --- |
| Total protein | 90.18 |
| Ash | 8.09 |
| Moisture | 5.14 |
| Solids | 94.86 |
| Collagen | 15.93 |
| Hyaluronic Acid | 2.00 |
| Elastin | 2.35 |

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention. In particular, it is to be understood that the present invention contemplates variations in the proteinaceous material, process parameters, including temperature, time, pH, salt (ash), separation techniques, drying or preparation techniques, and proteins of interest.

What is claimed is:

1. A solubilized protein composition obtained from avian eggshell membrane without the use of proteolytic enzymes or cross-linking agents, wherein the composition has an ash content of less than 10% by weight of the composition and a protein content of at least 50% by weight of the composition, wherein the composition comprises a mixture of solubilized proteins selected from the group consisting of Type I collagen, Type V collagen, Type X collagen, elastin, lysozyme, ovotransferrin, desmosine, and/or B-N-acetylglucosaminidase, wherein the solubilized proteins are undenatured and retain biological activity, and wherein the solubilized protein composition is obtained by a process comprising:
   (a) exposing the eggshell membrane to a sufficient amount of a basic solution for a sufficient length of time and temperature for hydrolysis of the eggshell membrane to occur so as to produce a solution containing solubilized proteins whereby the solubilized proteins are undenatured and retain biological activity;
   (b) cooling the solubilized protein solution to a temperature of from about 2° C. to about 18° C.;
   (c) centrifuging the cooled solubilized protein solution to form a supernatant liquid;
   (d) removing ash from the supernatant liquid so that the supernatant liquid has a conductivity of less than 5 milliSiemens/cm; and
   (e) recovering the solubilized protein composition from the supernatant liquid obtained in step (d) by filtering the supernatant liquid through a membrane that has a molecular cutoff of at least 100 kDa to obtain a retentate protein mixture containing solubilized proteins having a molecular weight of greater than 100 kDa and/or a permeate protein mixture containing solubilized proteins having a molecular weight of less than 100 kDa.

2. The composition of claim 1 wherein the composition comprises at least 15% collagen, at least 1% elastin, and at least 1% of hyaluronic acid.

3. The composition of claim 1 wherein the composition comprises as least 20% elastin.

4. The composition of claim 1, wherein the composition comprises a physiologically acceptable carrier.

5. The composition of claim 1, wherein the composition is formulated for use in medical, cosmetic, dermatological, nutritional or pharmaceutical applications.

6. The composition of claim 1, wherein the composition further comprises a polysaccharide selected from the group consisting of hyaluronic acid, chondroitin, and glucosamine.

7. The composition of claim 1, wherein the supernatant liquid is acidified to a pH from about 6.0 to about 8.0.

8. The composition of claim 1, wherein the pH of the solution during hydrolysis is from about 9.0 to about 11.5.

9. The composition of claim 1, wherein the pH of the solution during hydrolysis is from about 10.5 to about 11.5.

10. The composition of claim 1, wherein the composition has a protein content of at least 90%, by weight.

11. A beverage, food or nutritional product comprising the composition of claim 1.

12. The product of claim 11, which is intended for animal or human consumption.

13. A cosmetic, medical, nutritional, dermatological, or pharmaceutical product comprising the composition of claim 1.

14. A solubilized protein composition obtained from avian eggshell membrane without the use of proteolytic enzymes or cross-linking agents, wherein the composition is essentially odor-free, has an ash content of less than 10% by weight of the composition and a protein content of at least 90% by weight of the composition, wherein the composition comprises a mixture of solubilized proteins selected from the group consisting of Type I collagen, Type V collagen, Type X collagen, elastin, lysozyme, ovotransferrin, desmosine, and/or B-N-acetylglucosaminidase, wherein the solubilized proteins are undenatured and retain biological activity, and wherein the solubilized protein composition is obtained by a process comprising:
  (a) exposing the eggshell membrane to a sufficient amount of a basic solution for a sufficient length of time and temperature for hydrolysis of the eggshell membrane to occur so as to produce a solution containing solubilized proteins whereby the solubilized proteins are undenatured and retain biological activity;
  (b) cooling the solubilized protein solution to a temperature of from about 2° C. to about 18° C.;
  (c) centrifuging the cooled solubilized protein solution to form a supernatant liquid;
  (d) removing ash from the supernatant liquid so that the supernatant liquid has a conductivity of less than 5 milliSiemens/cm; and
  (e) recovering the solubilized protein composition from the supernatant liquid obtained in step (d) by filtering the supernatant liquid through a membrane that has a molecular cutoff of at least 100 kDa to obtain a retentate protein mixture containing solubilized proteins having a molecular weight of greater than 100 kDa and/or a permeate protein mixture containing solubilized proteins having a molecular weight of less than 100 kDa.

15. The composition of claim 14 wherein the composition further comprises a polysaccharide selected from the group consisting of hyaluronic acid, chondroitin, and glucosamine.

16. The composition of claim 14, wherein the supernatant liquid is acidified to a pH from about 6.0 to about 8.0.

17. The composition of claim 14, wherein the pH of the solution during hydrolysis is from about 9.0 to about 11.5.

18. The composition of claim 14, wherein the pH of the solution during hydrolysis is from about 10.5 to about 11.5.

* * * * *